United States Patent [19]

Vander Mey

[11] 4,335,079
[45] Jun. 15, 1982

[54] APPARATUS FOR THE SULFONATION OR SULFATION OF ORGANIC LIQUIDS

[76] Inventor: John E. Vander Mey, 78 Winding Way, Stirling, N.J. 07980

[21] Appl. No.: 198,779

[22] Filed: Oct. 20, 1980

[51] Int. Cl.³ .............................. B01J 3/02; B01J 10/02
[52] U.S. Cl. ................................... 422/194; 159/6 R; 159/49; 422/209; 422/210; 422/240
[58] Field of Search ............... 422/193, 194, 198, 209, 422/210, 234, 240, 241; 159/6 R, 6 W, 6 WH, 49; 233/3, 12, 13, 14 R, 21

[56] References Cited

U.S. PATENT DOCUMENTS

| | | | |
|---|---|---|---|
| 487,100 | 11/1892 | Seymour | 233/12 |
| 2,010,405 | 8/1935 | MacIsaac | 422/209 |
| 2,422,882 | 6/1947 | Bramley | 159/6 R |
| 2,724,549 | 11/1955 | Brown | 233/3 |
| 3,347,620 | 10/1967 | Yamashita | 422/209 |
| 3,371,059 | 2/1968 | Rich | 159/6 R |
| 3,476,310 | 11/1969 | Poppenberg | 233/12 |
| 3,775,062 | 11/1973 | Susuki et al. | 422/209 |
| 3,902,857 | 9/1925 | Vander Mey et al. | 422/209 |

FOREIGN PATENT DOCUMENTS 3907  9/1979  European Pat. Off. ............ 422/209

Primary Examiner—Bradley Garris
Attorney, Agent, or Firm—Clayton F. Smith

[57] ABSTRACT

A continuous process is disclosed which comprises introducing a sulfonatable or sulfatable organic liquid onto a rotating reaction surface as a thin film, rotating the reaction surface at a velocity such that the thin film is continuously moved toward the periphery of the reaction surface, dividing the reaction surface into a plurality of areas, depositing within each area a controlled quantity of gaseous sulfur trioxide over the liquid film, maintaining the pressure during the reaction at subatmospheric levels, controlling the temperature of the reaction surface, moving the reaction product by centrifugal action to the periphery of the reaction surface and continuously collecting the reaction product.

An apparatus for carrying out such a process is also disclosed.

15 Claims, 6 Drawing Figures

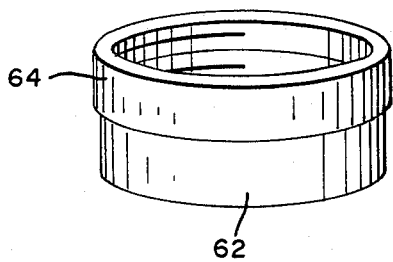
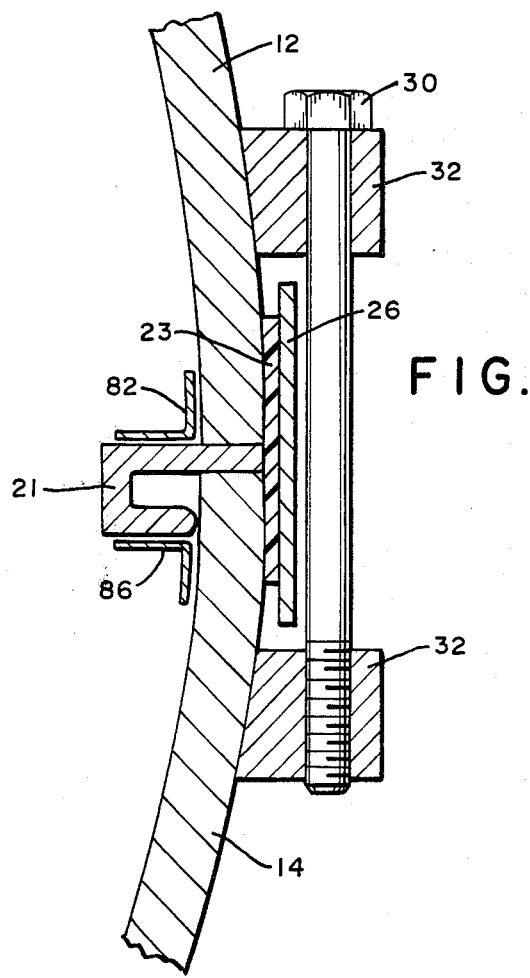

APPARATUS FOR THE SULFONATION OR SULFATION OF ORGANIC LIQUIDS

CROSS-REFERENCE TO RELATED APPLICATIONS

U.S. patents disclosing methods of sulfonating thin films of organic liquids by related means include U.S. Pat. No. 3,902,857 filed by John E. Vander Mey and Frank J. Kremers on Aug. 13, 1973 and U.S. Pat. No. 4,163,751, a division of the above, filed on Aug. 7, 1979.

BACKGROUND OF THE INVENTION

1. Field of the Invention

This invention relates to a process and to apparatus for reacting a thin film of an organic liquid with a gaseous medium under reduced pressure. In particular this invention relates to a process and apparatus for continuously reacting a sulfonatable or sulfatable organic liquid with sulfur trioxide.

2. Description of the Prior Art

In recent years several processes and several types of apparatus have been suggested for reacting thin films of sulfonatable and sulfatable organic liquids with sulfur trioxide. Hereinafter when reference is made to sulfonation processes and to sulfonatable materials, it is to be understood that sulfation processes and sulfatable materials are also included, where their inclusion is applicable.

As the need for developing more forms of energy has grown, sources of oil, once considered too difficult or uneconomical to recover have now assumed much greater importance. This fact has now provided great impetus for improving sulfonating processes and apparatus, for large quantities of sulfonated oil detergents are now used in the "tertiary" oil treatment for the recovery of residual oil from the ground, as can be obtained, for example, from otherwise exhausted oil wells.

This technique, also known as the "Marathon Process" is presently employed to recover some of the vast amount of oil still remaining in the ground. The process involves the use of large quantities of oil-soluble detergents for solubilizing oil remaining in the ground which has not been attainable by the methods used in the past.

But there are also many other uses for sulfonated organics, and whereas color is unimportant when sulfonated oil detergents are employed for oil recovery, the lack of color becomes important in the manufacture of detergents and surface active agents from alkyl aryl hydrocarbons or aliphatic alcohols. Where the final product is designed for household use, a colorless or substantially colorless product is of prime importance.

Sulfonation with sulfur trioxide has advantages over sulfonation procedures using oleum, but the reaction between sulfur trioxide and sulfonatable organic compounds is generally violent and difficult to control. The uncontrolled exothermic reaction provides an undesirable colored product, hence various means to control the reaction have been suggested.

Some of the suggested processes require large quantities of an inert carrier gas such as air, introduced at high velocities to move a thin film of organic liquid along a cooled surface during the reaction. Such processes require air compressors and dryers, becoming costly both because of equipment and power requirements.

A process and apparatus for reacting a thin film of an organic liquid with a gaseous reactant which minimizes the problems discussed above is described in U.S. Pat. Nos. 3,902,857 filed on Aug. 13, 1973, and 4,163,751, a division of the above, filed on Aug. 7, 1979. Another such process is disclosed in U.S. patent application, Ser. No. 285,382 filed Aug. 30, 1972, now abandoned.

It would be desirable, however, to provide an improved process and apparatus for reacting a thin film of an organic liquid with a gaseous sulfur trioxide in a manner to increase production, reduce the cost of operation, reduce the amount of plant space required and provide a high quality substantially colorless product. It would be desirable to provide a sulfonating apparatus so compact as to be readily constructed as a mobile unit, capable of movement to any location where a continuing supply of a sulfonated product is required. Further, it would be desirable to provide such a compact unit capable of still higher production rates in those instances where product color is of secondary importance.

SUMMARY OF THE INVENTION

The present invention is directed to an improved process for reacting a thin film of an organic liquid with a gaseous medium. The process comprises the steps of introducing the organic liquid onto the inner curved surface of a rotating spheroidal reaction chamber at is axis or polar area, rotating the reaction chamber at a velocity such that the organic liquid is continuously formed into a thin film on the curved reaction surface, dividing the film covered curved reaction surface into three or more successive concentric reaction areas, depositing over each reaction area a controlled amount of said gaseous medium to thereby control the rate of reaction as the liquid film proceeds from one curved reaction area to the next under the urging of centrifugal force, reacting the organic liquid and the gaseous medium stepwise, under subatmospheric pressure on the rotating curved reaction surface, moving the resulting reaction product to the equatorial region of the rotating reaction chamber, and collecting the reaction product from the equatorial region of the spheroidal reaction chamber.

The apparatus of this invention for reacting a thin film of an organic liquid with a gaseous medium comprises an oblate or substantially spheroidal reaction chamber mounted on a supporting frame for rotation on its axis in a substantially horizontal position, with an inner reaction surface; evacuating means for maintaining the reaction chamber under subatmospheric pressure; separating means to divide the reaction surface into successive reaction areas or segments, thus forming corresponding individual chambers to which the reaction areas are exposed; a first depositing means to deposit the organic liquid on the reacting surface, a second depositing means for depositing controlled quantities of the gaseous reactant within the individual chambers; rotating means to rotate the reaction chamber at a speed such that the organic liquid is continuously moved by centrifugal action as a thin film, successively, over the concentric reaction areas for exposure to the gaseous reactant, and the resultant reaction product is continuously moved to the inner periphery of the reaction chamber where it accumulates; cooling means for controlling the reaction temperature; and means for removing the reaction product from the reactor.

When the gaseous reactant is sulfur trioxide, this may be introduced as a substantially undiluted gas, with the subatmospheric pressure being maintained below 100 mm Hg, preferably below 25 mm Hg. The sulfur trioxide may also be introduced as a mixture of sulfur trioxide and an inert gas such as air. The output of a sulfur burner system designed to deliver "converter gas" of about 8% $SO_3$ may be used, and in fact satisfactory results may be obtained even if the $SO_3$ content is as low as 4%. With the employment of such low strength sulfur trioxide the subatmospheric pressure of the reaction chamber may be maintained at about one-half atmosphere or less. The process of this invention can therefore be operated successfully employing a gaseous sulfur trioxide of from about the concentration of "converter gas" to pure sulfur trioxide obtained from such sources as stabilized liquid sulfur trioxide, oleum, or other conventional sources. Preferably, substantially pure sulfur trioxide is used with the pressure within the reaction chamber maintained below about 25 mm Hg.

The process of my invention produces far less air pollution than is obtained from conventional sulfonating apparatus, less power is required, a small vacuum pump is employed rather than a large air compressor and only a small scrubber is required.

Still another advantage of the apparatus of my invention is that it is small, compact, produces a high quality product in good yield, and can be constructed as a mobile unit for ready removal to any point where the product is required.

Although the present invention may be used for a variety of chemical reactions between organic liquids and gaseous reactants, in a preferred embodiment of this invention the gaseous medium is sulfur trioxide and the organic liquid comprises a sulfonatable or sulfatable organic liquid.

BRIEF DESCRIPTION OF THE DRAWINGS

FIG. 4 is a perspective view of one type of screen diffuser which can be used between the separator discs to improve the uniformity of the distribution of the gaseous reactant within each separated chamber.

FIG. 6 of the drawings is a cross sectional view taken through 6—6 of FIG. 5.

DESCRIPTION OF THE PREFERRED EMBODIMENT

The process and apparatus of the present invention are particularly applicable in the sulfonation or sulfation by gaseous sulfur trioxide of appropriate organic liquids. Such compounds include saturated alcohols, phenols, olefinic compounds and monocyclic and polycylic aromatic compounds. For example, compounds suitable for sulfation by sulfur trioxide include those fatty acids containing 8 to 20 carbon atoms such as lauryl, myristyl and cetyl alcohol; ethoxylated derivatives of the above fatty acids and the ethoxylated derivatives of alkyl phenols wherein the alkyl group contains from about 8 to about 16 carbon atoms such as octene, decene, dodecene, tetradecene, hexadecene, etc; aromatic hydrocarbons such as those containing benzene, anthracene, or like structures and alkyl substituted derivatives thereof, such as toluene, ethylbenzene, dodecyl benzene, etc. The advantages of the present method of sulfonation are particularly evident in the production of alkyl aromatic sulfonic acids which when neutralized with an alkali metal hydroxide, an amine or an alkanol amine form highly effective detergent compounds. Thus the process of the present invention will be preferably applied to those alkylated aromatic compounds in which the alkyl groups contain a total of from 8 to 22 carbon atoms and in particular, 12 to 14 carbon atoms. In those instances where the organic compound is a solid at room temperatures, it may be preheated to the liquid state, or liquefied by any other desired procedure.

The sulfur trioxide used as the active ingredient may be obtained from any suitable source. It may be vaporized from stabilized liquid sulfur trioxide, obtained from oleum or from other conventional sources. When such gaseous sulfur trioxide is undiluted with other gases, the sulfonation or sulfation is preferably maintained at a subatmospheric pressure of below about 100 mm Hg, or better still, below 25 mm pressure Hg.

However, dilute sulfur trioxide is also applicable. Converter gas containing about 8% sulfur trioxide with the balance being air gives good results, and in fact the sulfur trioxide content can be as low as about 4%. In those instances where such a dilute sulfur trioxide is used, the subatmospheric pressure is maintained at about half an atmosphere (380 mm Hg.) or lower. With other dilutions of higher concentration, intermediate pressures would apply.

An important benefit offered by the present invention stems from its compact structure and relatively high product output. It is compact enough to be rendered mobile, and sulfonators made according to the principles here disclosed can be moved to wherever a supply of a sulfonated product is required. This is especially important today when sulfonated oils are of such importance in the recovery of oil from shale, exhausted oil wells and oil-bearing sands and tars.

Figure 1:
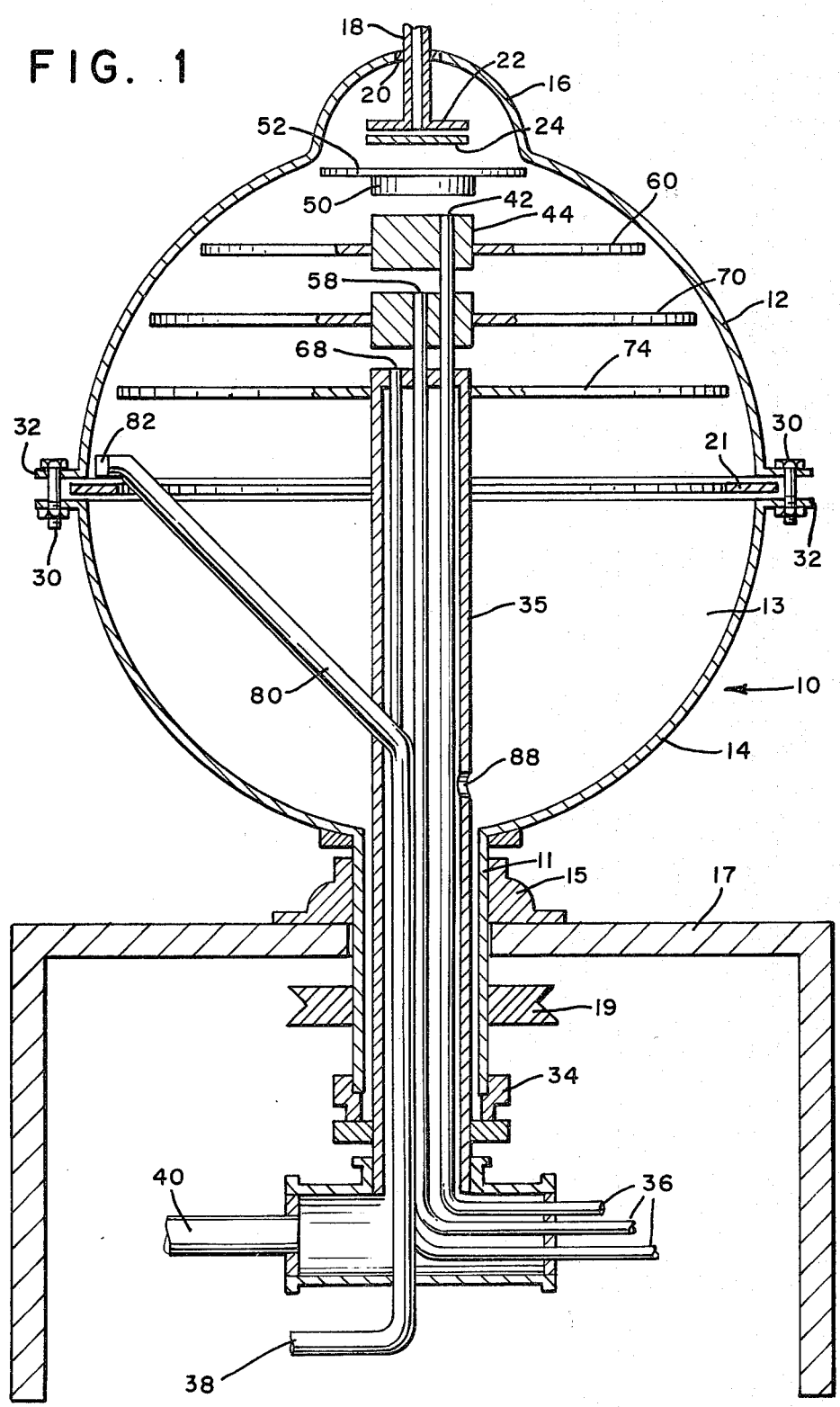
FIG. 1 of the drawings is a simplified cross sectional diagram of the rotary spherical reaction chamber of the present invention.
Figure 2:
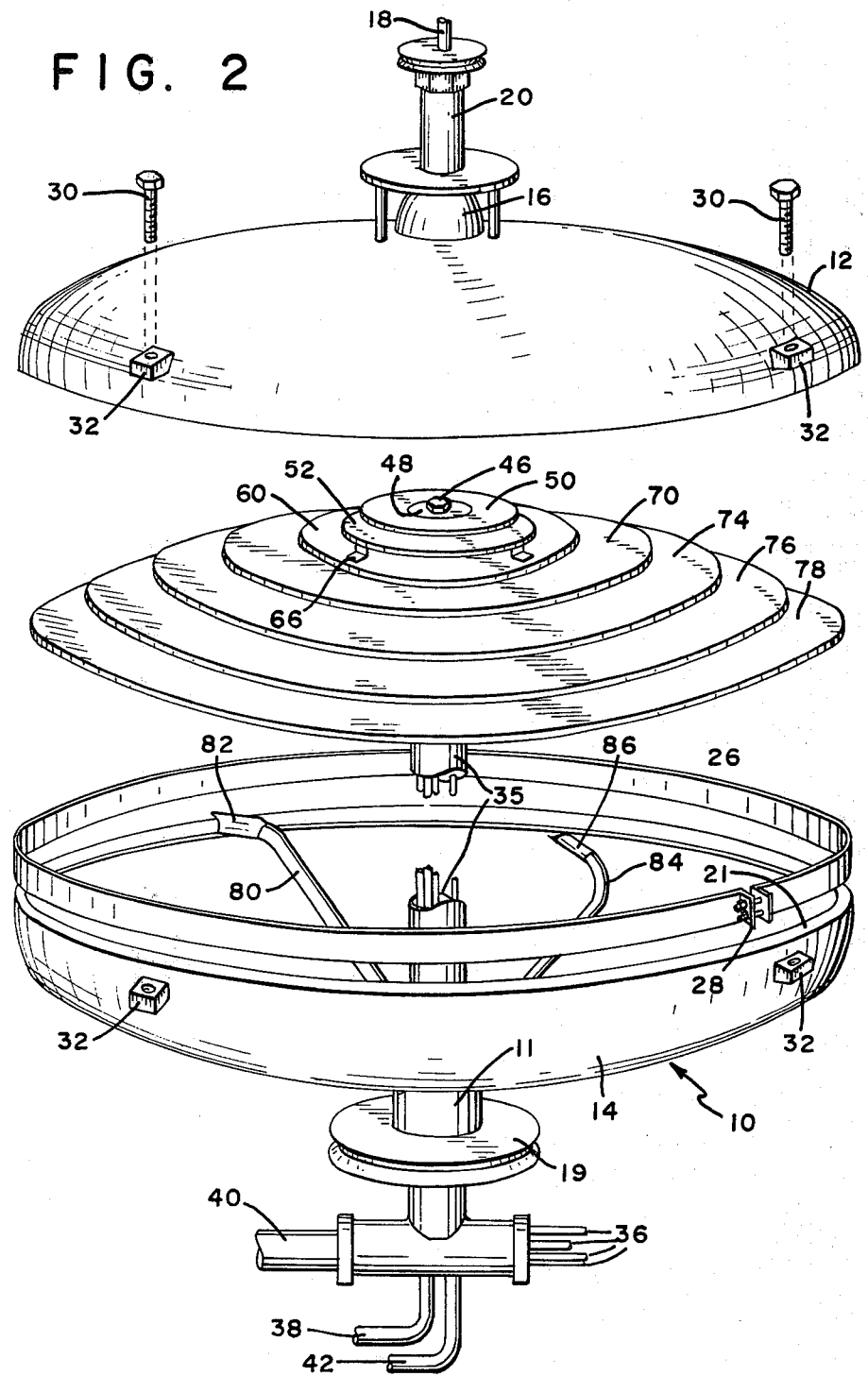
FIG. 2 is a partially exploded perspective view of the preferred embodiment of the present invention. This version has an oblate reaction chamber, the cross section being substantially eliptical. This drawing and those to follow are based on an actual prototype reactor.
Figure 5:
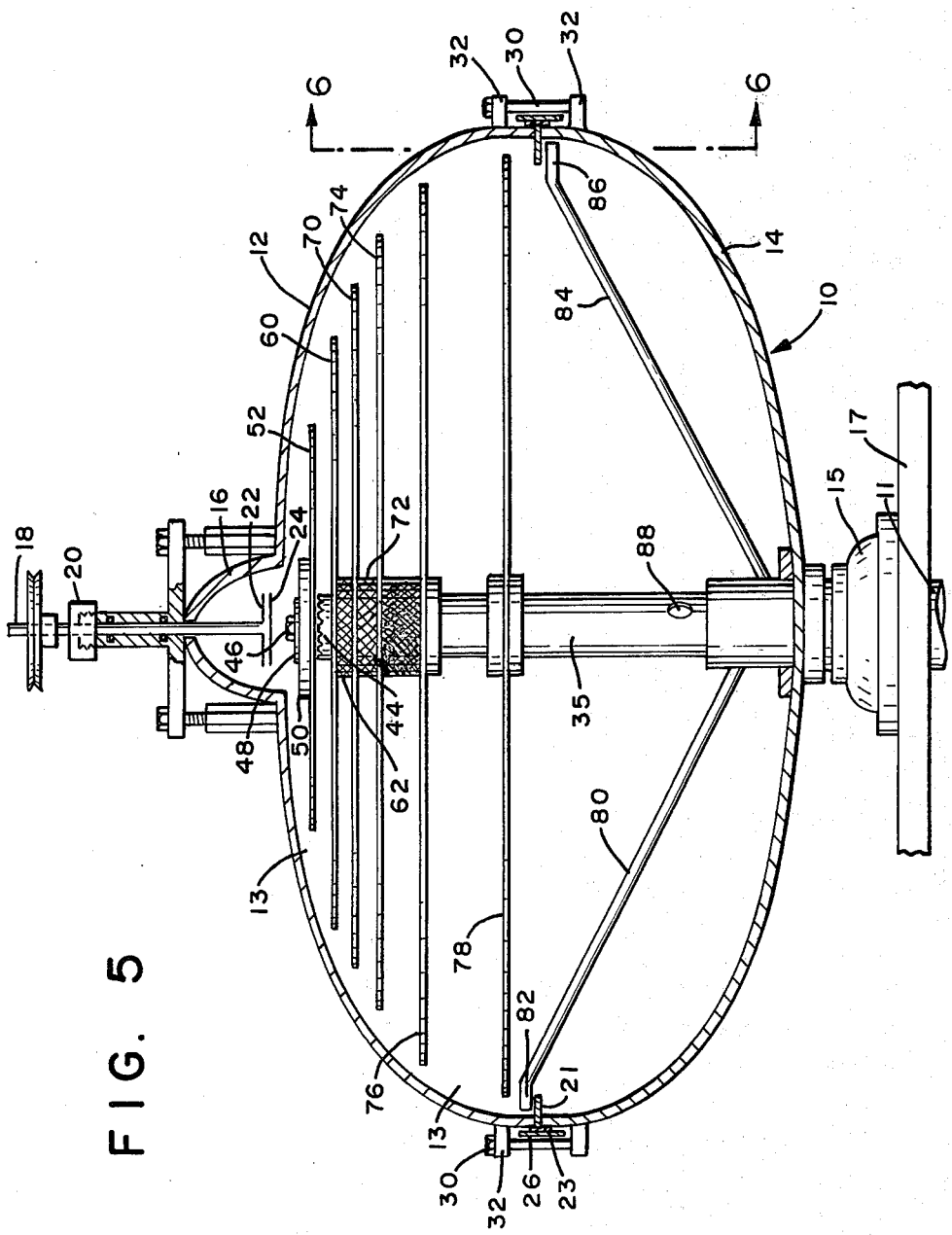
FIG. 5 is a cross sectional view in elevation of the assembled reaction chamber, being the same embodiment as the exploded view of FIG. 2.

With reference to the drawings of FIGS. 1, 2 and 5, there is shown as a preferred embodiment, a rotatable spherical, spheroidal or oblate sulfonation reactor indicated generally at 10. This includes reaction chamber 13 comprising hemispherical sections 12 and 14. These hemispheres are of a material such as stainless steel, resistant to the reactants to be employed. This is also true of all those surfaces which come in contact with the reactants, with the possible exception of a few small parts mentioned below which may be fabricated of a resistant polymeric material such as Teflon. In the prototype reactor, 304 stainless steel was found to be satisfactory.

When ready for assembly the rims or perimeters of these two hemispheres 12 and 14 are brought together, separated only by a metal product-collector ring 21 having an outside diameter substantially equal to that of hemispheres 12 and 14, but an inner diameter up to about 2 inches less than the inner diameter of the hemispheres at their perimeters.

In the prototype sulfonator those sections herein referred to as "hemispheres" are actually 42 inch dish heads of 7/32 inch 304 stainless steel. The stainless steel product collector ring 21 is a circle or ring of channel steel with the sides of the channel extending outwardly, with the uppermost side of the channel having an outside diameter equal to the outer diameter of the hemispheres, and the lower side of the channel having a diameter just under that of the inside diameter of the hemispheres so that when ready for assembly, the lower side of the channel will fit inside the rim of the lower hemisphere and the upper side of the channel will extend over the rim, lying gasket-like between the butted rims of both hemispheres. The inner diameter of this collector ring 21 in the prototype is about ¾ inch less than the inside diameter of the hemispheres at their rims so that the product-collector ring extends inwardly, ⅜ inch beyond the rims of the hemispheres. A clear view of the cross section of product-collector ring 21 as positioned in the prototype reactor is shown in FIG. 6. Although this is the preferred type of ring, a flat ring of sheet stainless steel would serve as well.

In the center of the bottom of the lower hemisphere 14 there is a circular opening at the perimeter of which is fixed a strong hollow shaft 11 extending downwardly from the reaction chamber. This shaft supports and rotates reaction chamber 13. Shaft 11 is journaled in bearing 15 shown fixed to supporting frame 17. Sheave 19 is fixed concentrically to the hollow shaft 11 below frame 17 whereby power transmitted from a motor not shown can rotate shaft 11 journaled at 15, and the reaction chamber 13 on a substantially vertical axis.

Hollow shaft 11 surrounds a stationary column 35 which extends below the rotary hollow shaft and is fixed with respect to supporting frame 17. The rotary hollow shaft 11 is journaled and sealed by a conventional ceramic-carbon mechanical seal 34. Such mechanical seals are marketed by the Crane Packing Co., and others. (FIG. 1)

This stationary column 35 also extends upwardly almost to the top of reaction chamber 13 and contains a plurality of conduits, 36 and 38. Extending from the lower end of this column are at least two tubes 36 for conducting sulfur trioxide up into the reaction chamber. Three are shown in FIG. 1, and four in FIGS. 2 and 3. If desired, still more can be used for fine reaction control, although about four is preferred. It would also be within the scope of the present invention to introduce the sulfur trioxide into the stationary column 11 through one conduit and use the column as a manifold to divide the sulfur trioxide into two or more streams within the column or as it leaves the column, within reaction chamber 13.

Also, extending from the lower end of the column is a product line 38 (FIGS. 1, 2 and 3), and a spent gas outlet 40 (FIGS. 1 and 2) which is connected with a small scrubber and vacuum pump, not shown. Still another conduit 41 (FIG. 2) can be included to withdraw any small amount of colored product which, if formed, can be collected in the lower hemisphere.

Preferably, one of the conduits of the group or bundle 36 extends to an opening 42 at the top of column 35 and enters a distributing head 44. In the preferred embodiment of the present invention, as shown in FIGS. 2 and 5, and detailed in FIG. 3, the upper portion of column 35 is shown as Teflon or any other suitable resistant material, and the conduits therein are cast or drilled within the solid Teflon. Stainless steel bolt 46 passing through stainless steel washer 48, Teflon disc 50 and stainless steel separator disc 52 engages threaded opening 54 to draw disc 52 tightly against distributing head 44. Sulfur trioxide or other gaseous reactant ascending a conduit, being one of the bundle 36 and escaping through opening 42 would be distributed by distributing head 44 through notches 56.

The type of distributing head is not essential. It can be a ring or cylinder of fritted glass, stainless steel, or a perforate ring of suitable material, stainless or Teflon woven screening, or it can be dispensed with entirely without affecting the end product to a marked degree.

In the embodiment of FIG. 1, Teflon disc 50 is adjacent to, and becomes a part of the distributing head; and the separator disc 52 is above rather than below it. Whether the Teflon disc 50 is above or below separator disc 52 is inconsequential.

Separator disc 52 has a diameter such that it leaves an annular space of no more than about an inch, preferably about a quarter of an inch between its perimeter and the adjacent wall of the upper hemisphere 12. Since the disc is attached to the stationary column 35, it too, remains stationary as the rotating reaction chamber turns about it.

Below separator disc 52 there is a second separator disc 60, also fixed to the stationary column 35. It is parallel to disc 52 and also extends almost to the wall of the upper hemisphere leaving an annular space of no more than about an inch, but preferably about one quarter of an inch. The vertical distance between the two discs is such that the annular area defined by these two circular separator discs comprises between about 5% and 15% of the total inner curved reaction surface of the upper hemisphere 12, or preferably about 7%.

The thickness of the circular separator discs is not critical provided they are heavy enough to remain substantially rigid. In the prototype sulfonator, 304 stainless steel was used having a thickness of 0.049 inches. Supporting separators 66 (FIGS. 2 and 3) can be employed if desired but are not essential.

Just below circular separator plate 60 there is an opening 58 in communication with a second conduit of the bundle 36, also for the introduction of the gaseous reactant such as sulfur trioxide.

Below circular separator disc 60 and opening 58 there is a third circular separator disc 70, also fixed to the column 35 at its center. It is parallel with separator disc 60 and also extends almost to the wall of the upper hemisphere leaving an annular space of no more than about an inch, preferably about one quarter of an inch.

The vertical distance between the two circular separator discs 60 and 70 is such, that the annular area of the wall or reaction surface defined by circular separator discs 60 and 70 comprises between about 7 to 20% of the total inner curved reaction surface of the upper hemisphere 12, or preferably about 10%.

Preferably a cylindrical screen 62 or porous or perforate cylinder surrounds column 35 between separator discs 60 and 70 to aid in producing an even distribution of the gaseous reactant leaving opening 58. Details of a suitable 304 stainless screen cylinder attached to a Teflon ring 64 is shown in FIG. 4. The inner surface of ring 64 can be threaded to cooperate with matching threads on column 35 for precise positioning of the distributing screen 62 (FIGS. 3 and 5) and for positioning separator disc 60.

Just below circular separator disc 70 there is another opening 68 in communication with a third conduit of the bundle 36, for the introduction of the gaseous reactant. Below this there is a forth circular separator disc 74 also fixed to the stationary column. It is parallel to discs 60 and 70 and extends almost to the wall of the upper hemisphere, also leaving an annular space of less than about one inch, preferably about one quarter of an inch.

The vertical distance between separator discs 70 and 74 is such that the annular area defined by separator discs 70 and 74 comprises between about 10% and 25% of the total inner curved reaction surface of the upper hemisphere 12, or preferably about 15%. As in the case of circular separator discs 60 and 70, preferably a cylindrical screen 72 (FIG. 5) or other type of distributor surrounds column 35 between separator discs 70 and 74.

Just below separator disc 74 in the case of the embodiment shown in FIG. 3, there is still another opening 75 in communication with the last conduit shown of the bundle 36 for the introduction of a gaseous reactant. Below this there is a fifth circular separator disc 76 also fixed at its center to the stationary column 35. It too, is parallel to discs 60, 70 and 74, and as with the latter, extends almost to the wall of the upper hemisphere 12, leaving an annular space of less than about an inch, preferably about one quarter of an inch. (FIGS. 2 and 5) The vertical distance between discs 74 and 76 is such that the annular area defined by separator discs 70 and 76 comprises between about 20 and 30% of the total inner curved reaction surface of the upper hemisphere 12, or preferably about 25%.

Figure 3:
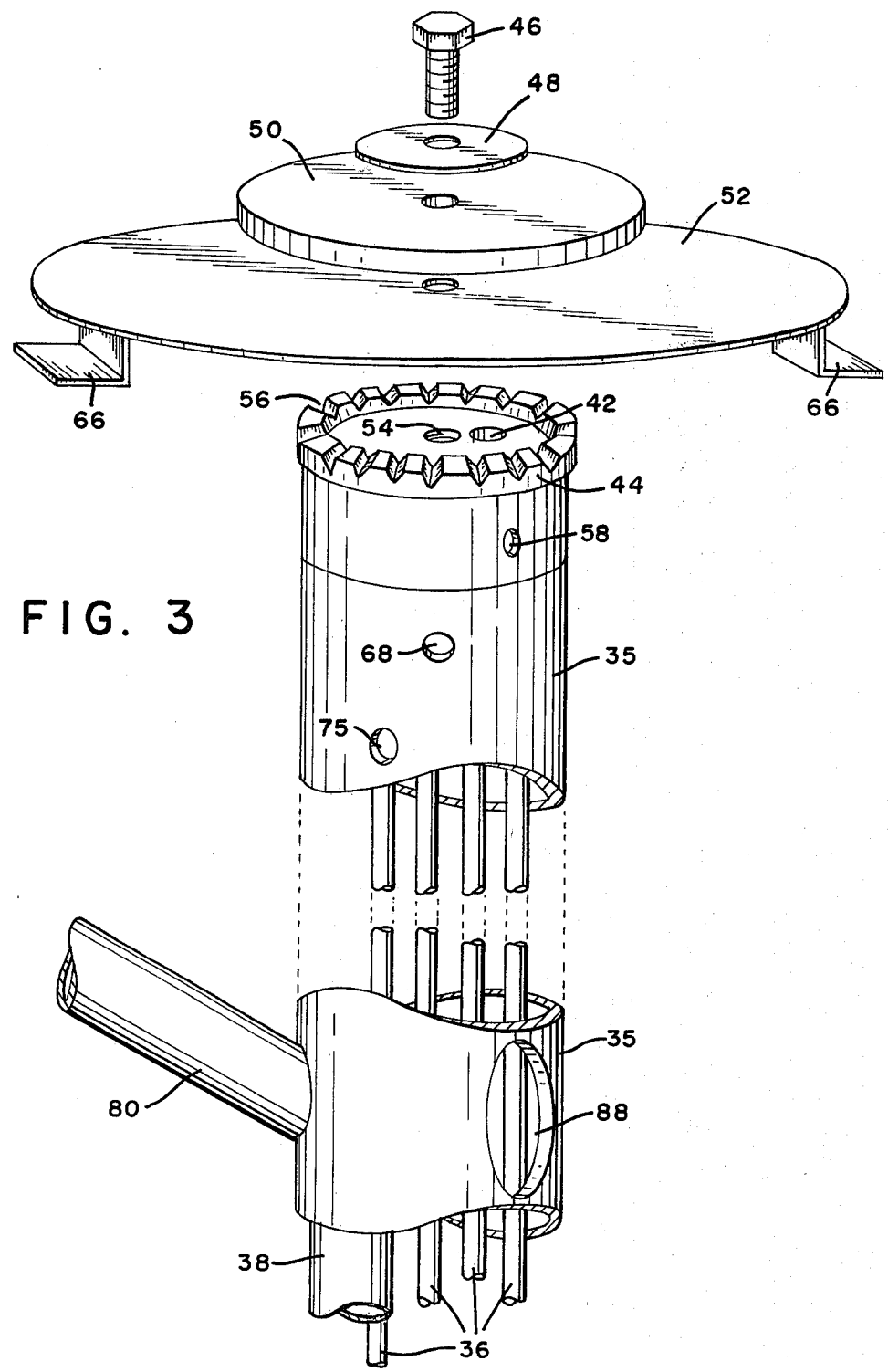
FIG. 3 is a broken, partially exploded view of a detail of the stationary central column through which the gaseous reactant enters, and the product is withdrawn.

The above circular separator discs divide the reaction surface into three concentric reaction zones in the case of the embodiment of FIG. 1, and into four concentric reaction zones in the modified reaction chamber of FIGS. 2,3 and 5. In the case of the preferred embodiment of FIGS. 2 and 5, still another circular disc 78 is shown, but this serves only as a baffle and not as a separator disc. It is positioned just above collector ring 21 and has a diameter between about one half inch to 4 inches less than the inside diameter of the product collecting ring 21 which is just below it. Preferably, the diameter is about 2 inches less than the inner diameter of the product collecting ring. Baffle disc 78 is not critical to the present invention but serves to prevent any oversulfonated mist from reaching the final colorless, or essentially colorless product.

Hollow shaft 11 to which the driving pulley 19 for the rotary reaction chamber 13 is fixed, is adjustable within limits, so that it may be raised or lowered, and with it, the entire reaction chamber which is fixed thereto. It is clear, then, that by thus raising or lowering the reaction chamber in relation to the fixed column 35 which supports the separator discs, the annular clearances of these circular discs, and the concentric areas of reaction surface can be altered within limits. The bearing 15 and the seal 34 permit this adjustment.

The amount of sulfur trioxide or other gaseous reactant that can be delivered to each of the partitioned spaces between the circular separator discs can be controlled. Each of the conduits of bundle 36 can have its own control valve, not shown, as does my prototype sulfonator. These control valves are preferably in communication with a manifold supplied with the reactant gas of the concentration and pressure desired. Further, each can have its own flow meter and even automated equipment which is readily available, to mechanically control the flow of gas, independently, to each partitioned space.

In the preferred embodiment there is fixed, at the top center of the upper hemisphere 12 a bubble or bell-shaped appendage 16, the lower edge of which is joined smoothly to a circular opening at the top center of the upper hemisphere 12, said circular opening having the same diameter as that of the skirt or perimeter of bubble 16. The inner surface of the bubble 16 and the inner surface of the upper hemisphere 12, which is the reaction surface, are preferably highly polished.

An inlet feed pipeline 18 for the introduction of the organic liquid to be reacted with a gaseous reactant such as sulfur trioxide, passes through an opening in the top center of bubble 16 where it is journaled for longitudinal rotation. It is preferably supplied with suitable bearings for high speed rotation and passes through a substantially pressure-tight seal 20. Rotatable inlet feed pipeline 18 is in communication with a stationary conduit, the connection being made through a gas tight seal into which pipeline 18 is journaled. The conduit communicating with rotatable pipeline 18 is in communication with a controlled source of the liquid feed to be sulfonated or sulfated.

The lower end of feed line 18 terminates perpendicularly between two parallel discs, the diameter of which can be approximately half the diameter of the walls of the bubble 16 at its perimeter. Feed line 18 is sealed into a central opening in the first disc, the second disc of substantially the same diameter, being blank. These parallel discs are fastened together at three or more points. The vertical distance between these discs is related to the size of the sulfonator and to the amount of organic liquid to be fed into the reaction chamber. Assuming that the diameter of the feed inlet pipeline is chosen to be commensurate with the rate of flow of organic liquid to be handled, the distance between the discs is preferably about one quarter of the diameter of the feed inlet pipeline 18, or less. If desired, the parallel discs can have a plurality of perpendicular radiating impeller blades, straight or curved, as in a centrifugal pump, but these are not essential. Other types of spinning distributor heads can be used. A very effective type consists of two to four or more tubes in communication with the feed pipeline and radiating outwardly and perpendicularly from it. These may extend quite close to the wall of the bubble, being perpendicular to it, or they may turn away from their direction of rotation so as to be substantially parallel to the wall of the bubble and close to it.

Other types of spinning distributors are also satisfactory such as a hollow disc, sphere, or other shape having openings in its perimeter through which the liquid feed can be distributed by centrifugal force to the walls of the bubble. Furthermore, the bubble itself could be eliminated, with the distributing head dispersing the liquid feed directly into the top of the upper hemisphere 12.

A sheave is fixed to the rotary inlet feed pipeline 8 for driving the distributing head 22 and 24. The spinning distributing head is spun at an appreciably greater speed than that of the rotary reaction chamber, and preferably in the direction opposite to that of the rotary reaction chamber to insure uniform distribution of the liquid organic reactant.

There is also provided a product take-off line 80 terminating in a scoop 82 to collect product as it builds up as a result of centrifugal force above product collector ring 21. The take-off line 80 conducts the product to a take-off pump, not shown, for removal. A lute, not shown, can be included in the line to insure a good seal. A gear pump for product removal is preferred. The pump can deliver the product to a product receiver not shown. Alternately, the receiver can be maintained at a subatmospheric pressure to thus eliminate the need for a pump.

In FIG. 5 there is shown as an option, a discolored product take-off line 84 with scoop 86 positioned to collect any material collected below the collecting ring 21 coming from the lower hemisphere 14. An important feature of my invention is that all reacting surfaces face downwardly as well as inwardly, so that any mist formed which would not benefit from the cooling of the reaction surface, and would therefore be prone to overheating, over sulfonation and discoloration, would not fall back to the reaction surfaces, but would rapidly fall, because of the subatmospheric pressure, to the upper surface of the separator discs 60,70,74 or 76, or to the upper surface of baffle disc 78. All such material ultimately reaching the baffle disc would drop through the annular space surrounding baffle disc 78, to lower hemisphere 14. Here it would collect because of centrifugal force, below collector ring 21. So little such discolored product would be accumulated that it could easily be recovered from the bottom of the reactor after a short run, but the scoop 86 and discolored product take-off line 84 are shown in FIGS. 2 and 5 for the continuous removal of discolored product during a prolonged run, thus a novel method of continuously removing the bulk of substantially colorless product, and the small amount of discolored product, is provided. Any discolored product recovered can be combined with the main product when color is not critical, but kept separate where a colorless product is desired for use in household detergents and the like.

Recycling of any incompletely sulfonated product is easily accomplished by pumping all or part of the product back to feed line 18, but with all the adjustments provided, variation of the area of the several reaction surfaces, adjustment of the several streams of gaseous reactant and of the amount of liquid feed, incomplete sulfonation need not be encountered.

The opening 88 in the stationary column 35 of FIGS. 1,3 and 5, leads to the scrubber and vacuum pump not shown. It is the outlet for spent gas and provides the means for maintaining the system under reduced pressure.

When the reactor is to be closed, a band of suitable gasket material 23 of FIGS. 5 and 6, surrounds the juncture of the two hemispheres 12 and 14, so that the resulting reaction chamber 13 can be maintained at subatmospheric pressures. This band 23 is surrounded in turn by steel bellyband 26 of FIGS. 2,5 and 6, with a simple tightening device 28 of FIG. 2.

The hemispheres 12 and 14 are bolted together by two or more bolts passing through aligned drilled projections 32 fixed to the sides of each hemisphere.

In operating the equipment as in sulfonating a sulfonatable oil, the reaction chamber is evacuated. If substantially pure sulfur trioxide is to be used, a pressure of less than about 100 mm Hg is maintained, preferably between about 4 and 25 mm Hg. The oil is then introduced through feed inlet pipeline 18 while the feed line and disc distributor head 22-24 is spun at high speed. The sulfonatable oil is introduced into the reaction chamber while it is revolving in the direction opposite to that of the distributor 22-24 at a velocity of between about 25 and 400 RPM, preferably between about 100 and 200 RPM.

The liquid feed is thrown against the almost vertical polished inner wall of the bubble 16, and by centrifugal force, flows as a thin uniform film over the polished curved reaction surface toward the collector ring 21 at the equator or inner periphery of the rotating reaction chamber 13. In doing so it passes consecutively over the concentric annular areas separated by the circular separator discs 52, 60, 70, 74 and 76. Separate streams of sulfur trioxide, preferably independently controlled, are delivered to each partitioned chamber. Within each chamber the atmosphere provided does not supply sufficient sulfur trioxide to more than partially sulfonate that portion of the film of organic liquid momentarily exposed to that gaseous reactant. As the film of organic liquid flows over the annular reaction surfaces and passes one partitioned chamber after another, the ordinarily rapid reaction is slowed down. By the time it passes over the annular reaction surface exposed to the gaseous reactant between circular separator discs 74 and 76, the sulfonation has been virtually completed.

During the continuous process, zone heating or cooling as required is provided exteriorly by cold water jets or sprays, heated or cooled water or air, or heat lamps. The sulfonated product forced toward the reactor's inner perimeter collects above the collector ring 21 where it is continuously scooped up by scoop 82 of product line 80 and preferably directed to a gear pump and product receiver not shown. A product receiver maintained at subatmospheric pressure may be employed rather than a gear pump if desired.

A small sulfonator such as the 42 inch (diameter) prototype could be expected to produce between about 250 and 350 lbs of high quality product per hour. Any discolored product which may form from mist as previously explained could, if present in sufficient quantity, be scooped up by scoop 86 of pipeline 84 of FIG. 2 and collected by a separate gear pump and/or receiver not shown.

When treating highly viscose or solid sulfonatable materials, they can be fluidized by preheating, and if necessary, heat lamps or other sources of radiant energy can be used initially on the reaction surface.

The primary aim of this process and apparatus is to produce an essentially colorless high quality product. However, for some sulfonated products such as the sulfonated oils of value in the Tertiary process for the recovery of oil from exhausted oil wells, shales and oil bearing sands, color is of little concern.

Where there is no need for the separation of darkened product, no collector ring is required within the reaction chamber. The product can be scooped from the inner periphery or equator of the rotating reaction chamber.

It is also possible, where color in the product is of no consequence, to operate the apparatus in an inverted position with the reaction chamber suspended downwardly from its driving mechanism, or constructed as shown, but with the liquid organic feed and the partitioning separator discs being located in the lower hemisphere. The reaction chamber can also be fabricated and operated with a set of separator discs in each of the two hemispheres, with or without baffle discs, and with the fluid organic feed entering through rotating distributors at both poles of the rotating reaction chamber. The inner surface of both hemispheres is preferably a highly polished surface, and no collector ring is then required. The sulfonated product is continuously scooped from the inner periphery of the apparatus.

Quite apart from the use of the apparatus described as a sulfonator, it has also been found effective as a flash evaporator, either at atmospheric or subatmospheric pressures. Because of the thin film of liquid distributed over the evaporating surface, and the low evaporating temperatures possible, especially when the apparatus is used as a vacuum flash evaporator, products ordinarily discolored or chemically altered by heat can be effectively concentrated or evaporated in the apparatus described.

It will be apparent that the process and apparatus of my invention will permit the continuous production of an especially high quality product at a reasonably high rate of production, and this from a small compact apparatus which could be handled as a mobile unit and moved to those locations where a continuous supply of such product is required.

It is to be understood that variations and modifications of the present invention may be made without departing from the scope of this invention. It is also to be understood that the scope of the invention is not to be interpreted as limited to the specific embodiment disclosed herewith, but only in accordance with the appended claims when read in the light of the foregoing disclosure.

I claim:

1. A rotatable reactor for reacting a thin film of an organic liquid with a gaseous reactant comprising an oblate or substantially spheroidal reaction chamber mounted on a supporting frame for rotation on its axis in a substantially horizontal position, with an inner reaction surface; evacuating means for maintaining said reaction chamber under subatmospheric pressure; separating means comprising a plurality of parallel discs to divide said reaction surface into successive reaction areas, thus forming corresponding individual chambers to which said reaction areas are exposed; said discs being perpendicular to said axis of rotation, a first depositing means to deposit said organic liquid on said reaction surface, a second depositing means for depositing controlled quantities of said gaseous reactant within said individual chambers; rotating means to rotate said reaction chamber at a speed such that said organic liquid is continuously moved by centrifugal force as a thin film, successively over said successive reaction areas for exposure to said gaseous reactant, and the resultant reaction product is continuously moved to the inner periphery of said reaction chamber where it accumulates, cooling means for controlling the reaction temperature; and means for removing said reaction product from the reactor.

2. A reactor as claimed in claim 1 including means to prevent small amounts of darkened product from combining with the main body of reaction product, and means to remove said small amounts of darkened product from the rotating reactor while it is in operation.

3. A sulfonation apparatus comprising a spheroidal rotatable reaction chamber having upper and lower hemispheres, a hollow shaft fixed thereto and in communication with said chamber, said hollow shaft being journaled into a supporting base and connected to means for rotating said shaft and attached reaction chamber about a substantially vertical axis of rotation, said shaft surrounding the lower portion of a stationary column extending upwardly substantially to the top of the upper hemisphere within said rotatable reaction chamber, said hollow shaft being rotatable about said stationary column and said column having an opening within the rotatable reaction chamber in communication with gas pumping means for evacuating said reaction chamber, said stationary column containing at least three gas conveying pipelines in communication with controlled sources of a gaseous reactant, each one of said gas conveying lines terminating at its upper end in an opening in said stationary column with each of the said openings being positioned at a different level but within said upper hemisphere, said stationary column having attached to it a plurality of parallel discs, one just above the uppermost opening in said column, one just below the lowermost opening and one between each of the remaining openings, each of said discs encircling the stationary column with its diameter such that it extends substantially to the inner wall of the upper hemisphere at the particular level at which it is attached to the stationary column; and below the lowest of said discs at the perimeters and juncture of said upper and lower hemispheres of said reaction chamber there is positioned a collector ring having an inner diameter less than the inner diameter of the reaction chamber at the juncture of said hemispheres, and above said collector ring and adjacent to the inner wall of said upper hemisphere, is positioned a stationary scoop with its leading edge extending in the direction opposite to the direction of rotation of said rotatable reaction chamber, said scoop being in communication with a liquid product conveying line, sloping downward and entering said stationary column, said liquid product conveying line being in communication with pumping means for continuously collecting liquid product accumulating above said collector ring, said scoop being supported in its stationary position above said collector ring by the liquid conveying line and said stationary column to which said line is attached; and above the said parallel discs and at the top of said upper hemisphere there is journaled for independent axial rotation an inlet fluid conveying pipeline terminating in a fluid dispersion means, said fluid conveying pipeline being in communication with a source of supply of a liquid reactant, and with means for delivering said liquid reactant through said rotating dispersion means whereby said liquid reactant can be thrown outwardly by centrifugal force and evenly distributed on the inner wall of the upper hemisphere near its pole, to flow as a thin uniform film through concentric bands of reaction surfaces of the inner wall of the upper hemisphere, separated by said parallel discs, for reaction with the controlled gaseous reactant leaving the several openings in said stationary column between said parallel discs, and whereby said product of the reaction will move to the collector ring by centrifugal force for collection and continuous removal by said scoop, said liquid product conveying line and said pumping means.

4. An apparatus in accordance with claim 3 wherein the collector ring has an inside diameter of about from ½ to 3 inches less than that of the inner diameter of the reactor at its equator, while the outside diameter of the collector ring may be equal to the inner diameter of the reactor chamber at its equator.

5. An apparatus in accordance with claim 3 having heat exchange means to effect heating or cooling of the reaction chamber exteriorly as determined by the nature of the chosen reactants.

6. An apparatus as claimed in claim 3 including means to recycle said liquid reaction products to said reaction surfaces.

7. The apparatus as claimed in claim 3 including diffusion means through which said gaseous reactant passes after escaping from the plurality of openings in the stationary column.

8. The reactor as claimed in claim 3 wherein the collector ring fixed at the equator of the reaction chamber comprises an extending lip of a circular seal which serves to connect two symmetrical convex dish heads at their rims to form said spheroidal rotatable reaction chamber.

9. The apparatus in accordance with claim 3 in which the entire inner reaction surface of the reactor chamber is smooth and polished.

10. The apparatus in accordance with claim 3 wherein the inlet fluid conveying pipeline and dispersion means comprises a rotatable inlet pipeline axially journaled for independent rotation in a small hemispherical bubble-shaped appendage to said upper hemisphere, its perimeter being sealed to a centrally located opening of equal perimeter in the top center of said upper hemisphere, said inlet pipeline terminating just above the perimeter of the bubble-shaped appendage in a concentric circular dispensing means having about half the diameter of the bubble-shaped appendage at that point and having a plurality of openings in its perimeter, whereby on feeding liquid reactant through the inlet pipeline while spinning the pipeline, the liquid is thrown against the nearly vertical walls of the hemispherical bubble-shaped appendage, to then form a thin uniform film on the sidewall of the upper hemisphere as a result of its rotation.

11. An apparatus in accordance with claim 10 wherein said inlet pipeline terminates just above the plane of the perimeter of said bubble-shaped appendage in a juncture with at least two radially positioned tubes, each of which is in communication with said inlet pipeline, and each of which extends outwardly toward the walls of said bubble-shaped appendage, said tubes being angled away from the direction of rotation of said inlet pipeline, each tube to thereby terminate close to the walls of said bubble-shaped appendage and substantially parallel thereto, whereby on feeding liquid reactant through the inlet pipeline while it is spinning, the liquid is thrown against the nearly vertical walls of the hemispherical bubble-shaped appendage, to then form a thin uniform film on the sidewall of the upper hemisphere as a result of its rotation.

12. An apparatus in accordance with claim 10 wherein the concentric circular dispensing means at which said inlet pipeline terminates, comprises a first and second disc of substantially identical diameters, separated by spacers, said inlet pipeline being sealed perpendicularly to the first disc at a central opening having approximately the same diameter as the inside diameter of the inlet pipeline, the second disc, parallel to the first and having no central opening, is separated from the first by a distance of about one-fourth or less of the diameter of the inlet pipeline, said rotatable inlet pipeline being rotatable at a higher speed than the rotatable reaction chamber and in the direction opposite to that of said reaction chamber.

13. The apparatus in accordance with claim 10 in which the reaction chamber is fabricated of suitable corrosion resistant material, said upper hemisphere and the bubble-shaped appendage having smooth polished inner surfaces with a smooth rounded juncture between said bubble-shaped appendage and said upper hemisphere.

14. An apparatus in accordance with claim 10 wherein there is additionally, a second stationary scoop, this one being positioned below said collector ring and adjacent to the inner wall of the rotatable reaction chamber near its periphery, said scoop having its leading edge extending in a direction opposite to the direction of rotation of said rotatable reaction chamber, said scoop being in communication with a second liquid product conveying line being in further communication with pumping means for continuously collecting any low grade product accumulating below the collector ring.

15. The apparatus in accordance with claim 10 wherein said product collecting scoop in communication with its liquid conveying line is also in communication with a product receiver maintained under subatmospheric pressure.

* * * * *